(12) United States Patent  
Joyner

(10) Patent No.: US 9,789,006 B2  
(45) Date of Patent: Oct. 17, 2017

(54) PRESSURE BANDAGE

(71) Applicant: Cardiac EP Education and Innovation, LLC, Richmond, VA (US)

(72) Inventor: Charles A. Joyner, Richmond, VA (US)

(73) Assignee: Cardiac EP Education and Innovation, LLC, Richmond, VA (US)

( * ) Notice: Subject to any disclaimer, the term of this patent is extended or adjusted under 35 U.S.C. 154(b) by 216 days.

(21) Appl. No.: 14/504,754

(22) Filed: Oct. 2, 2014

(65) Prior Publication Data

US 2016/0095755 A1 Apr. 7, 2016

(51) Int. Cl.
| | | |
|---|---|---|
| *A61F 13/00* | (2006.01) | |
| *A61F 5/34* | (2006.01) | |
| *A61F 5/30* | (2006.01) | |
| *A61F 13/14* | (2006.01) | |

(52) U.S. Cl.
CPC .......... *A61F 13/00068* (2013.01); *A61F 5/30* (2013.01); *A61F 5/34* (2013.01); *A61F 13/14* (2013.01); *A61F 2013/00102* (2013.01); *A61F 2013/00119* (2013.01); *A61F 2013/00127* (2013.01)

(58) Field of Classification Search
CPC ................ A61F 13/00; A61F 13/00004; A61F 2013/00089; A61F 2013/00102; A61F 2013/00119; A61F 2013/00127; A61F 5/012; A61F 5/30; A61F 5/34; A61B 17/132; A61B 17/1322; A61B 17/1325; A61B 17/135

USPC .............. 602/13, 19, 41, 42, 53, 60, 75, 79; 606/201, 202; 128/118.1
See application file for complete search history.

(56) References Cited

U.S. PATENT DOCUMENTS

| 2,661,776 | A | * | 12/1953 | Gamber | ................. | D03D 15/08 |
|---|---|---|---|---|---|---|
| | | | | | | 139/383 R |
| 5,235,975 | A | | 8/1993 | Gang | | |
| 5,383,893 | A | * | 1/1995 | Daneshvar | ................. | A61F 5/34 |
| | | | | | | 128/118.1 |
| 5,514,155 | A | | 5/1996 | Daneshvar | | |
| 5,779,657 | A | | 7/1998 | Daneshvar | | |
| 5,843,008 | A | | 12/1998 | Gerhard | | |
| 5,891,070 | A | | 4/1999 | Shirouzu | | |
| 6,971,252 | B2 | * | 12/2005 | Therin | .................. | A61F 2/0045 |
| | | | | | | 66/170 |

(Continued)

FOREIGN PATENT DOCUMENTS

WO WO 2006069548 7/2006

*Primary Examiner* — Keri J Nelson  
(74) *Attorney, Agent, or Firm* — Finnegan, Henderson, Farabow, Garrett & Dunner, LLP

(57) ABSTRACT

A pressure bandage comprising an elastic band having a first end comprising a pocket member and a second end that is removably attachable to the first end. An inflatable bladder is placed in the pocket member and provides a substantially uniform pressure over a wound area when the band is placed on a patient and the bladder is inflated. The bladder is connected to a tube element which is used to inflate the bladder to the desired pressure. The elastic band may include a shoulder strap and may wrap over a patient's shoulder, across the patient's chest, and under the patient's opposite arm. The bottom side of the elastic band (facing the patient) may be made of a soft, absorptive material, and the bottom side of the pocket member may include an expandable mesh.

17 Claims, 7 Drawing Sheets

(56) References Cited

U.S. PATENT DOCUMENTS

| | | |
|---|---|---|
| 8,500,670 B2 | 8/2013 | Hansen |
| 2002/0084295 A1* | 7/2002 | Martindale .............. A45C 1/04 |
| | | 224/219 |
| 2010/0179586 A1 | 7/2010 | Ward |
| 2012/0232578 A1 | 9/2012 | Altobelli |
| 2013/0096475 A1 | 4/2013 | Guldalian |
| 2013/0110019 A1* | 5/2013 | Hopman .............. A61B 17/135 |
| | | 602/13 |
| 2014/0277102 A1* | 9/2014 | Mansur, Jr. .......... A61B 17/135 |
| | | 606/202 |

\* cited by examiner

PRESSURE BANDAGE

FIELD OF THE DISCLOSURE

The present invention relates to a pressure bandage for reducing pacemaker and ICD wound complications.

BACKGROUND OF THE INVENTION

Each year over 1 million pacemaker and implantable cardioverter defibrillator (ICD) implants are performed around the world. Each implant carries multiple risks, one of the most frequent of these being hematoma formation, which occurs anywhere from 2-5% of cases. Hematoma (localized bleeding) increases discomfort, dramatically prolongs healing time and hospital stay, raises the risk of infection at the site, and is disappointing to both patient and physician alike.

Moreover, the risk of these bleeds may be increasing as patients are often maintained on anticoagulant and antiplatelet medications through the entire procedural timeframe. Hematomas are now regarded as a measurable complication that can affect a physicians' quality metrics and reimbursement. In fact, Centers for Medicare & Medicaid Services (CMS) has included this as such.

Common practice is to simply place a sterile dressing with adhesive tape over the wound area, with or without icepack or weight on top. This may be inexpensive but it is awkward and the tape removal painful. Furthermore, the adhesive tape may cause in allergic reaction in the patient's skin. The addition of an arm sling offers little benefit, and if kept in place too long, it may cause shoulder joint problems such as adhesive capsulitis that can require weeks of physical therapy.

This practice has evolved little or over the past 2 decades. These and other drawbacks exist.

DETAILED DESCRIPTION OF THE EMBODIMENTS

In order that the invention herein described may be fully understood, the following detailed description is set forth. Various embodiments of the invention are described in detail and may be further illustrated by the provided examples. Additional viable variations of the embodiments can easily be envisioned.

Unless defined otherwise, all technical and scientific terms used herein have the same meaning as those commonly understood by one of ordinary skill in the art to which this invention belongs.

As used in the description herein and throughout the claims that follow, the meaning of "a," "an," and "the" includes plural reference unless the context clearly dictates otherwise.

The present invention is drawn to a pressure bandage to focus pressure on fresh pacemaker and defibrillator implant sites to decrease post-operative wound complications. The pressure bandage comprises an elastic band having a shoulder strap component. A pocket is integrated on a portion of the elastic band, and an inflatable bladder rests inside the pocket. An attachment mechanism is located at each end of the band and is configured to connect the ends of the band together when the band is wrapped around the chest of the patient. The bladder may be inflated and placed over the wound area to apply a substantially uniform pressure over the surface area of the wound. This could also be utilized for hemostasis of newer subcutaneous ICD implant and other postoperative sites. The entire mechanism may be fairly light. In one embodiment, the entire pressure bandage weighs ~1 lb. In an alternate embodiment, the pressure bandage may include a secondary strap.

Figure 1:
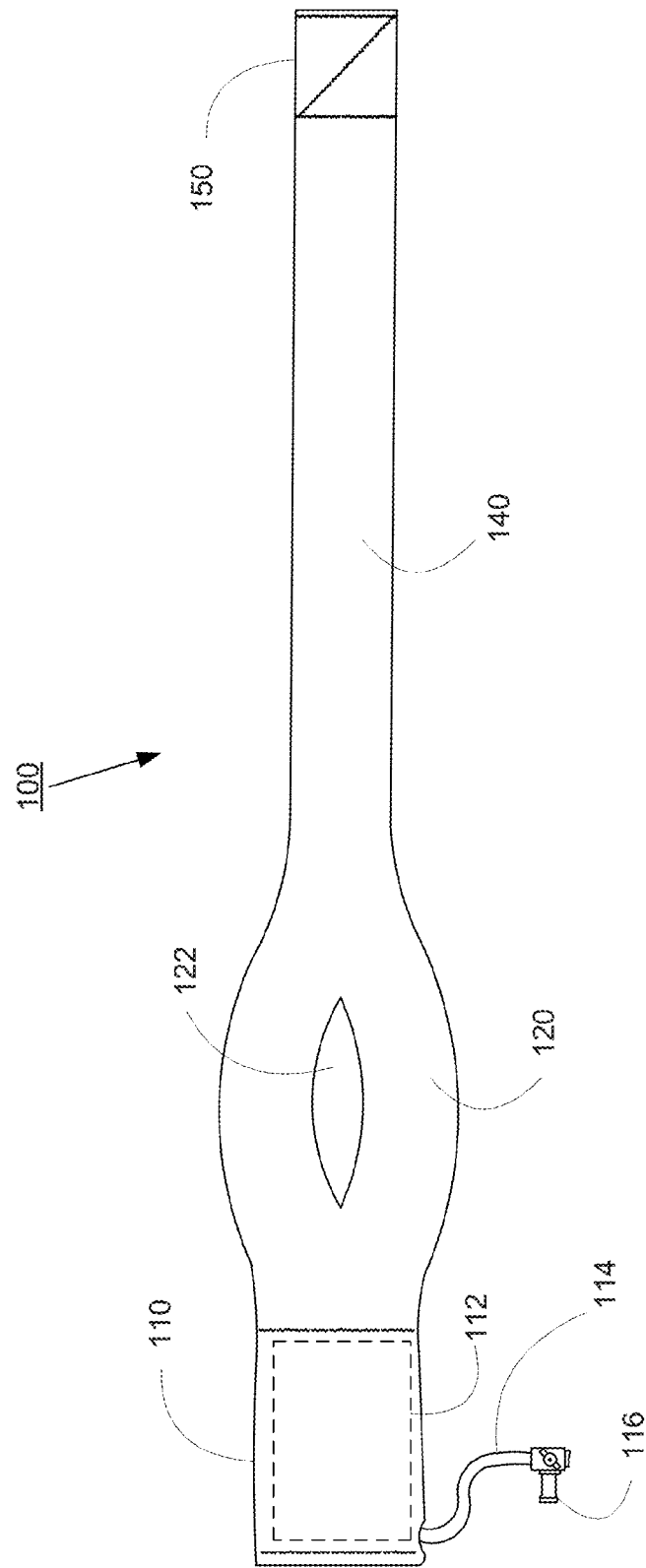
FIG. 1 depicts a schematic diagram of a pressure bandage, according to an example embodiment.
Figure 2:
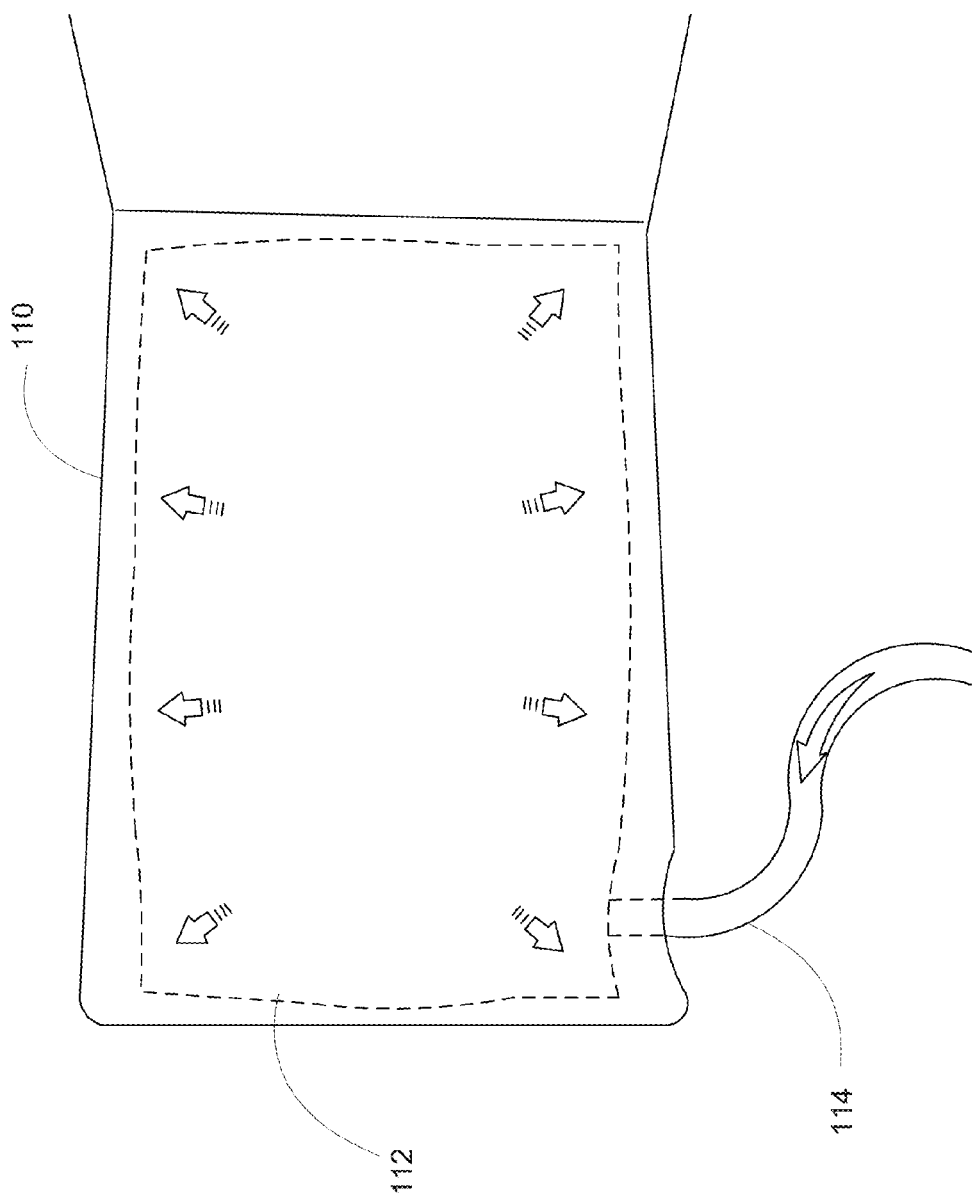
FIG. 2 is a schematic diagram of the inflatable bladder of the pressure bandage, according to an example embodiment.
Figure 3:
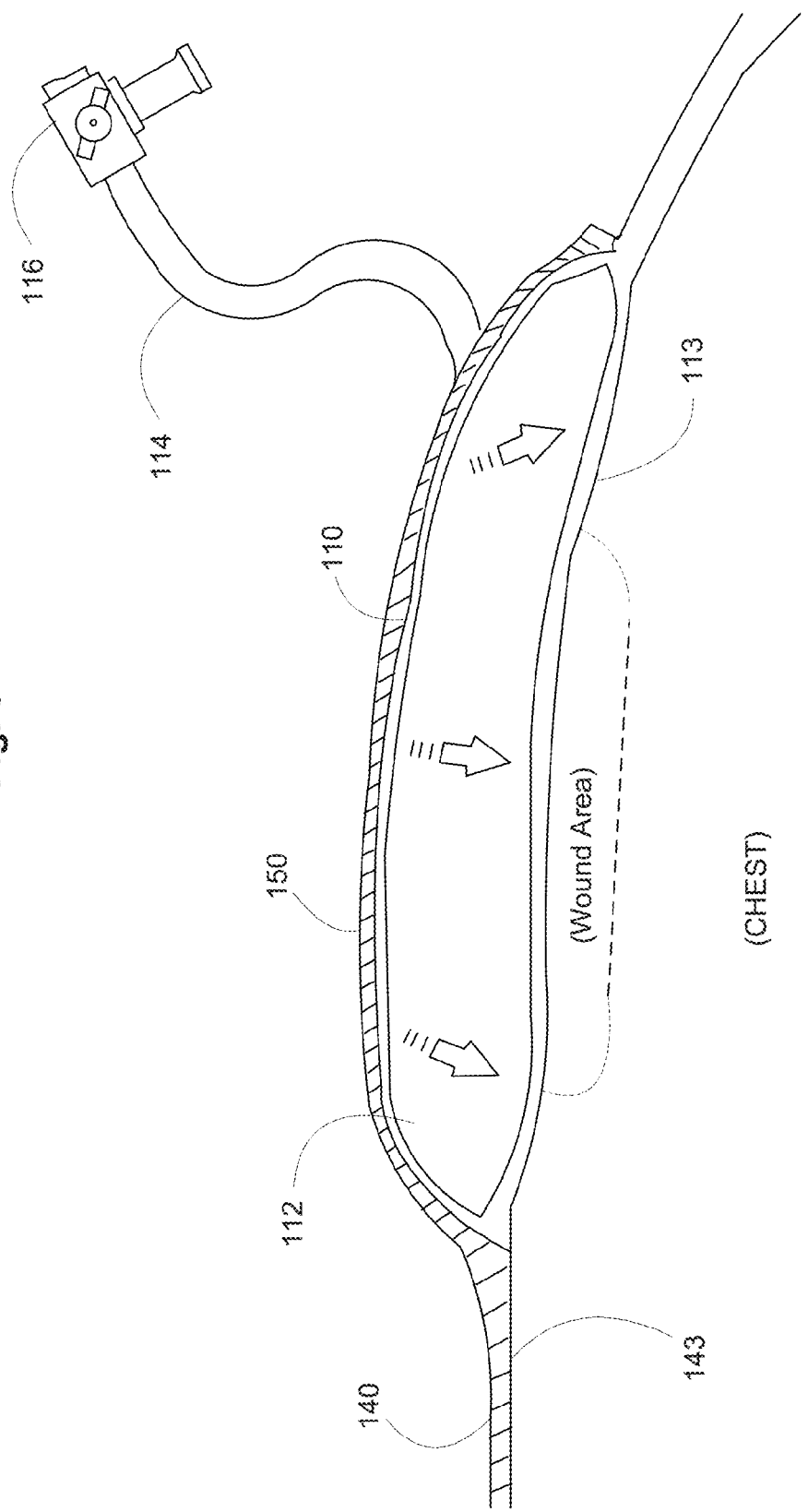
FIG. 3 is a schematic diagram of the inflatable bladder of the pressure bandage, according to an example embodiment.
Figure 4:
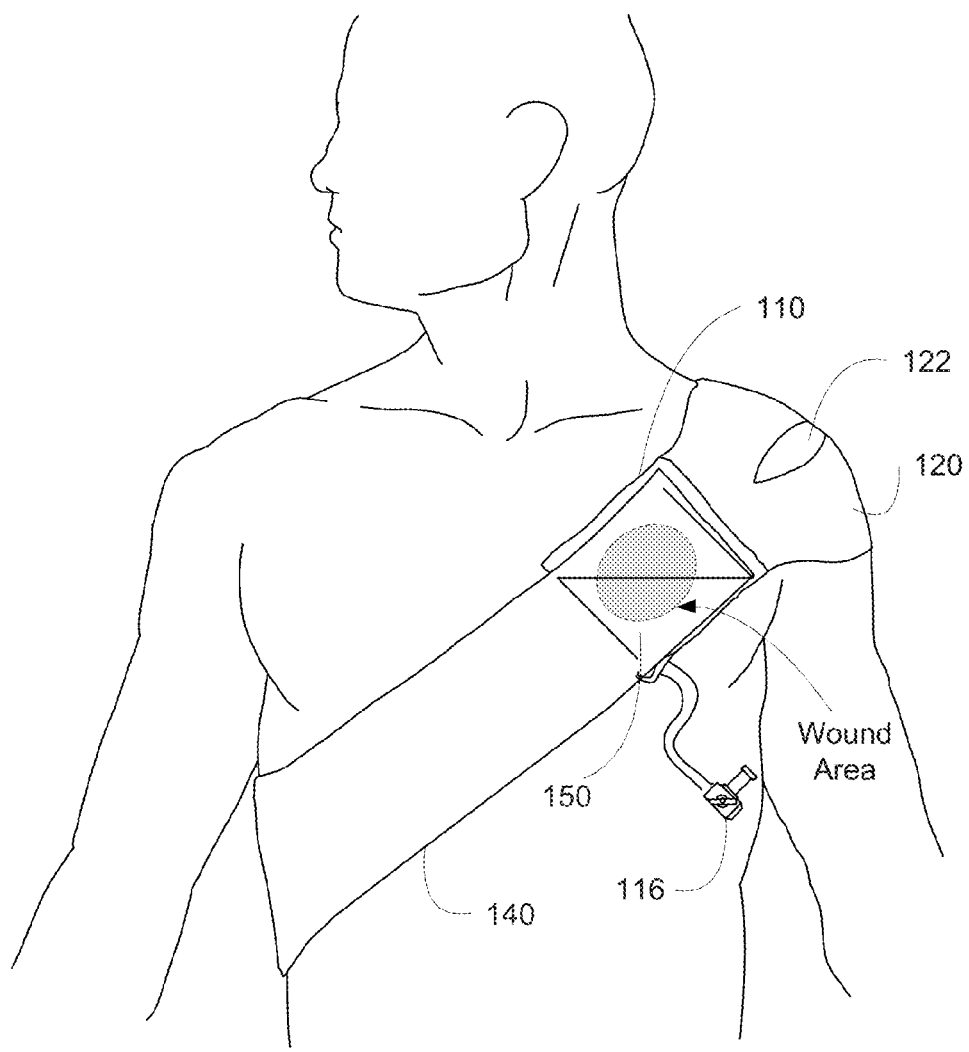
FIG. 4 is a schematic diagram of a pressure bandage, according to an example embodiment.

Proceeding now to a description of the drawings, FIGS. 1-4 depict an exemplary embodiment of the pressure bandage 100. FIG. 1 shows a top-down view of pressure bandage 100. The pressure bandage may comprise a band 140, a shoulder strap 120, a pocket member 110, and an attachment mechanism 150. The band 140 and shoulder strap component 120 may be made of an elastic material. Non-limiting examples of the elastic material include non-latex elastic yarn, and/or a cotton and polyester blend. In one embodiment, the band 140 may measure about 5 inches wide. In one embodiment, the length of pressure bandage 100 may be approximately 40 inches in an unstretched state. The bottom surface 113 of the pocket member 110, and the bottom surface 143 of the band 140 (shown in FIG. 3) may comprise a comfortable mix of material. Bottom surfaces 113 and 143 may be absorbent. Bottom surfaces 113 and 143 may comprise a non-adhesive, soft, absorptive surface. When the pressure bandage is wrapped around the patient (as shown in FIG. 4), the surfaces 113 and 143 may be in direct contact with the patient's skin, hence the need for a material that will minimize aggravation and discomfort.

The pocket member 110 may be configured to receive an inflatable bladder 112. Pocket member 110 may have a bottom side (i.e., the side facing the patient) and a top side. FIG. 2 depicts a view of the top side of pocket member 110. In one embodiment, the inflatable bladder 112 may be a square, rectangular, oblong, or circular in shape. In one embodiment, the inflatable bladder 112 is 5×6 inches. The inflatable bladder 112 may be connected to a 3-way stopcock 116 via a tube element 114. A medical syringe or pump may connect to the 3-way stopcock 116 and inflate the bladder 112. In another embodiment a removable, squeezable pump ball with or without an integrated valve may inflate the bladder. The bottom surface 113 of the pocket member 110 may comprise an expandable mesh pocket which may provide-space to hold ice packs and/or extra packing.

When inflated, the bladder 112 may be approximately 2 inches thick. In one embodiment, the bladder 112 may be inflated with air to 2-inch thickness via 3-way stopcock and typical medical syringe. The bladder 112 may be inflated to approximately 20 mm Hg-40 mm Hg of pressure. When inflated, the bladder 112 may exert light to moderate pressure on the surface area of a post-operative wound. The substantially rectangular shape of the bladder 112 provides substantially even pressure over the wound area on the patient's chest, as shown in FIGS. 2 and 3. The bladder 112 may completely cover the incision, as well as the area under the incision ("pacemaker or ICD pocket") where the device was inserted. In this way, when the bladder 112 is inflated, it provides precise pressure where it is needed.

In other embodiments, the pocket member 110 may be filled with padding, such as gauze pads, and not with the inflatable bladder 112. In practical use, providers may choose to utilize such padding and forego bladder inflation at their discretion. The tube 114 may connect to bladder 112 as a single, unitary piece. The tube 114 may be removeably connected to the bladder 112. Element 116 may comprise a valve that is removeably connected to the opposite end of tube 114 (e.g., using threaded ends). Element 116 may be a luer lock.

When inflated, the compressed area covered by the bladder 112 may range from 16 square inches to 36 square inches. In one embodiment, when inflated, the bladder 112 may cover an area of approximately 30 square inches. A pacemaker incision may cover 3-5 square inches, while a defibrillator may cover a much larger surface area. The bladder 112 may inflate in a substantially-even manner to avoid concentrated pressure at the center of the bladder which merely forces swelling outside the compressed area.

Attachment mechanism 150 is located at one end of pressure bandage 100. Attachment mechanism 150 may include a Velcro® (e.g., a hook and loop fastener) surface on the bottom surface 143 of pressure bandage 100. The top surface of pocket member 110 may include a Velcro® (e.g., a hook and loop fastener) surface that meshes with the bottom surface of attachment mechanism 150 when pressure bandage is placed on an individual, as shown in FIGS. 3 and 4. In other embodiments, attachment mechanism 150 may include a clip, a buckle, or some combination of the two.

Shoulder strap 120 may include a more elastic component 122 in the center of the strap 120. Elastic member 122 may ensure that strap 120 remains in a fixed in position at that point on the patient, so that pressure bandage 100 will not slide out of place, as shown in FIG. 4.

As shown in FIGS. 3 and 4, the pressure bandage 100 may be applied to a patient following implantation of a pacemaker or defibrillator device as follows: (1) Positioning pocket member 110 over the operative site; (2) Progressively wrapping shoulder strap 120 around ipsilateral shoulder and proceeding diagonally around the back with elastic band 140, and then wrapping around chest under the contralateral arm; (3) Stretching elastic band 140 to allow attachment mechanism 150 to meet the surface over the top of pocket member 110; (4) The complimentary surfaces are then allowed to attach via the hook and loop fasteners. The wound area incision is typically around 3 cm, but could be up to 7-8 cm. The wound area under the incision generally resembles a pocket where the pacemaker or defibrillator device is placed. This space under the incision can bleed if no compression is applied. The air bladder 112 acts to create substantially even pressure across the entire wound area, as shown in FIGS. 3 and 4. In most cases, the pressure applied by the inflated bladder 112 is roughly equivalent to the pressure that would be applied by placing a person's hand over the wound area. In some cases, the pressure may be approximately 20-40 mm Hg. As desired by the provider, ice pack or extra dressing can be placed in the mesh pocket. If more pressure is needed, or to conform to irregularities in patient anatomy, air is then injected into the bladder 112 to improve compression.

The bandage 100 can be left in place for hours or longer as desired. Unlike the arm sling that is commonly employed, arm motion is only minimally limited, thus increasing patient comfort in another manner. Patients can be discharged with the bandage 100 in place, potentially eliminating the need for an overnight stay and decreasing health care costs. A patient will generally wear this anywhere from a few hours to overnight, or longer as deemed appropriate by qualified provider.

Figure 5:
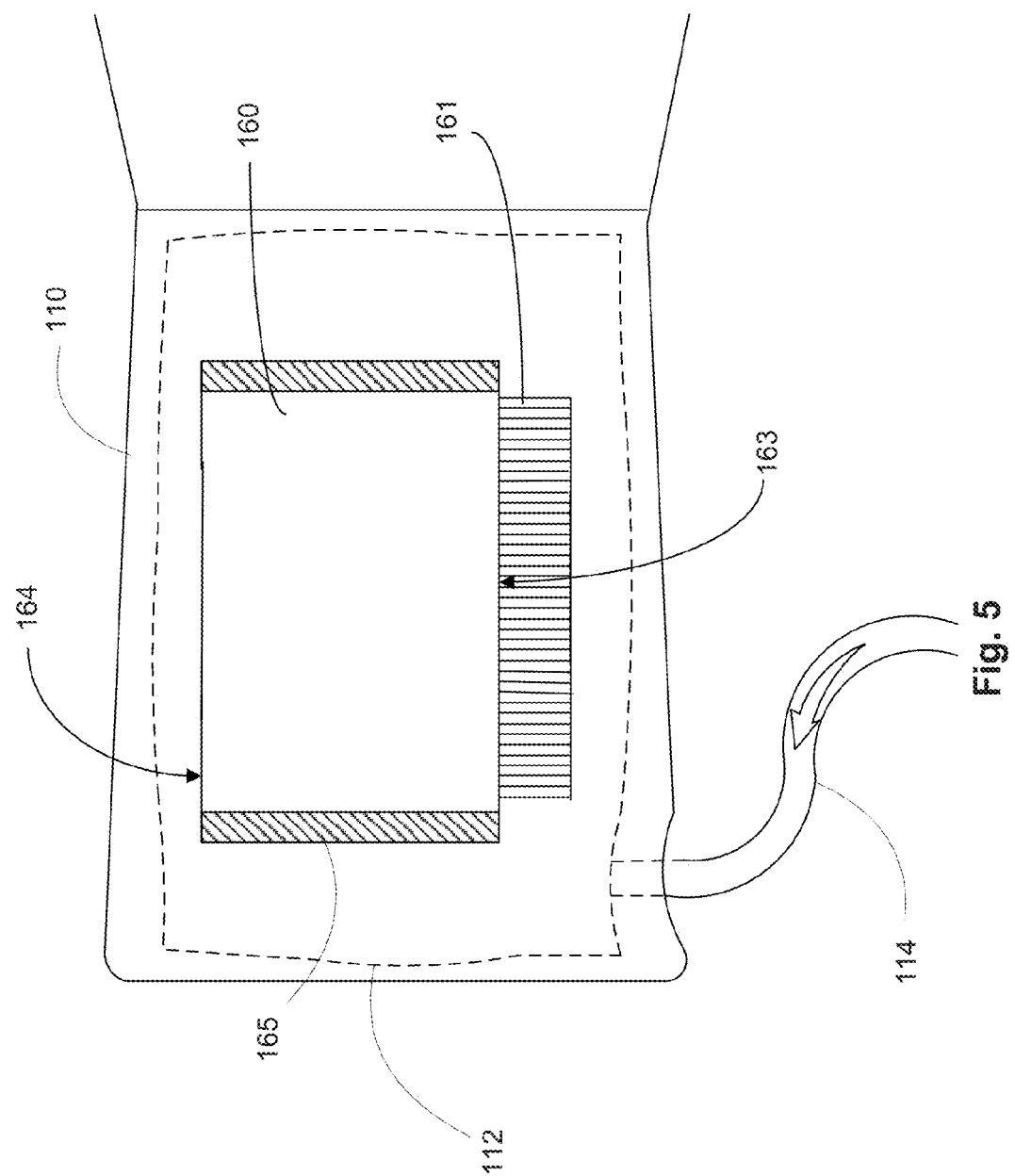
FIG. 5 is a schematic diagram of a pressure bandage having a secondary strap, according to an example embodiment.
Figure 6:
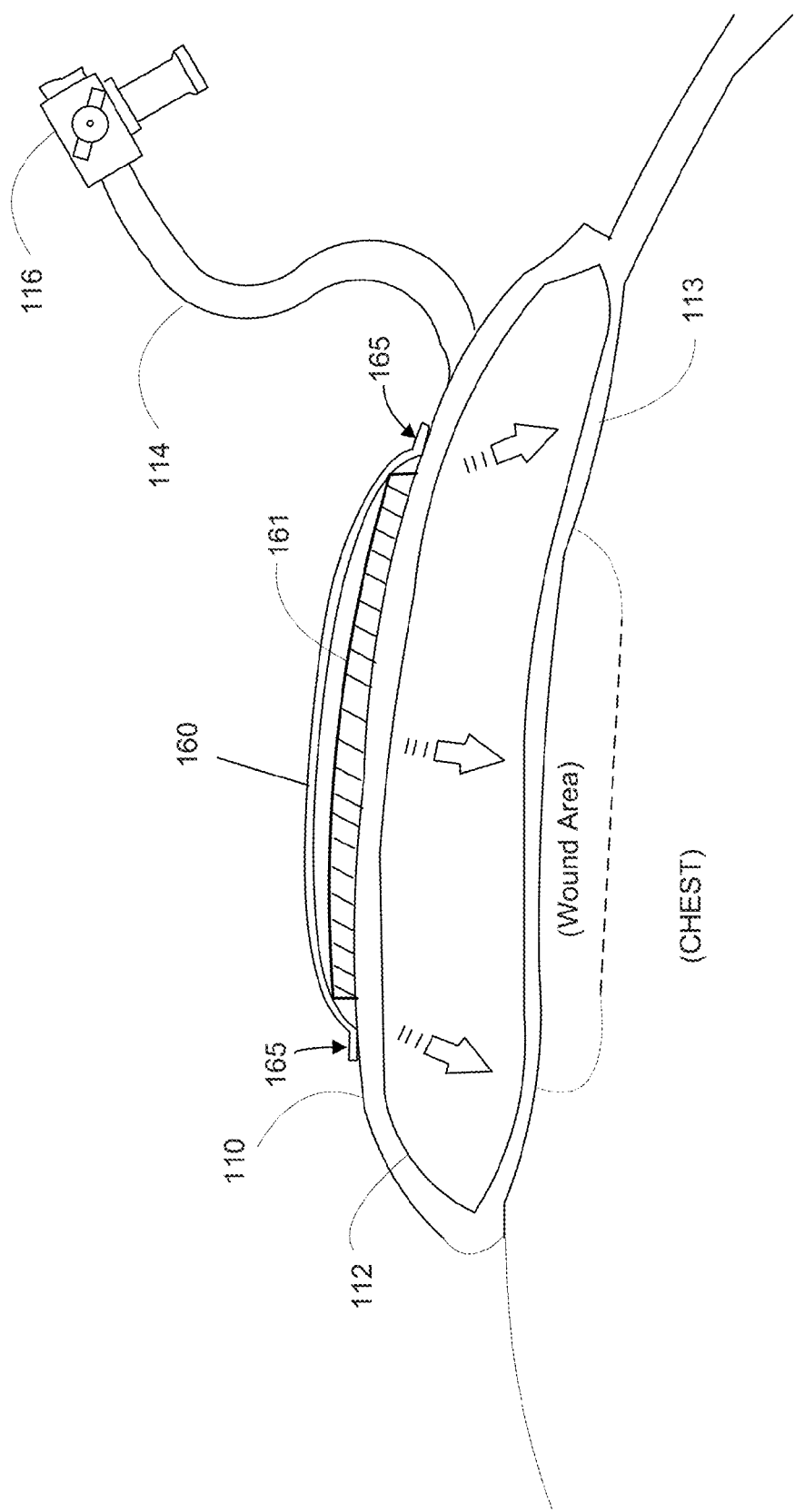
FIG. 6 is a schematic diagram of a pressure bandage having a secondary strap, according to an example embodiment.
Figure 7:
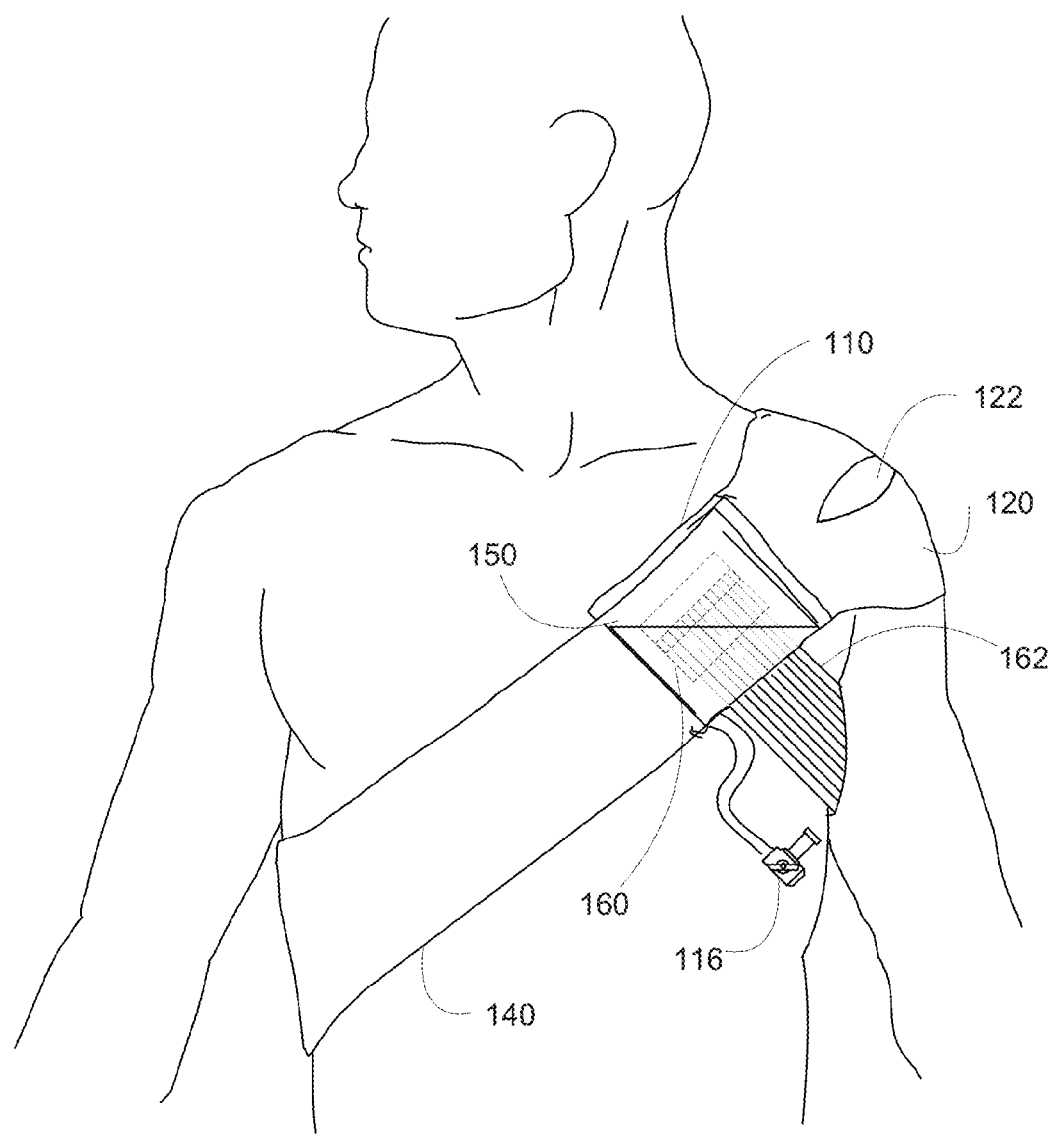
FIG. 7 is a schematic diagram of a pressure bandage having a secondary strap, according to an example embodiment.

FIGS. 5-7 depict an exemplary embodiment of the pressure bandage 100 having a secondary strap 162. In various embodiments, the secondary strap may provide more supportive, inward pressure on a wound area. In one non-limiting example, the secondary strap may provide additional pressure on the inferior aspect of a pacemaker or ICD pocket. Additionally, the secondary strap help maintain optimal positioning of the pressure bandage 100.

FIG. 5 shows a top-down view of a pressure bandage 100 (similar to the view in FIG. 2) having a secondary pocket 160 on the top surface of pocket member 110 (i.e., the surface facing away from the patient's chest). The secondary pocket 160 may comprise a square or rectangular-shaped piece of material that may be attached to the top of pocket 110 using stitching 165 at opposite ends. The ends 164 and 163 of secondary pocket 160 may be open. Secondary strap 162 may be made of an elastic material and may be folded and concealed under pocket 160 when not in use. Secondary strap 162 may be made of the same or similar material as elastic band 140. Secondary strap 162 may be deployed from secondary pocket 160 via either the first opening 163 or the second opening 164, depending on whether the pressure bandage is used on a left sided pacemaker or ICD implant (as shown in FIGS. 4 and 7) or on a right sided pacemaker or ICD implant.

Secondary strap 162 may comprise a tab 161 at one end. The underside of the tab 161 may include hook and loop fasteners (e.g., Velcro®). In one embodiment, secondary strap 162 may be approximately 4 inches wide and 4-6 inches long in an unstretched state. In one embodiment, secondary strap 162 may be configured to stretch to over twice its unstretched length. When deployed, secondary strap 162 may be pulled via tab 161 from under secondary pocket 160 through opening 163, stretching section 162 around the chest under the axilla (armpit) and around part of the back. Tab 161 may be attachable to a portion of band 140 at the patient's back.

In one embodiment, tab 161 may contain an approximate 0.75 inch×4 inch band of Velcro® (e.g., a hook and loop fastener) material allowing attachment to a middle segment of band 140. This same hook and loop fastener would anchor tab 161 in place on top surface of pocket member 110 in the undeployed state (under secondary pocket 160). The other end of strap 162 (opposite tab 161) may be anchored with stitching to the middle of the top surface of member 110 under secondary pocket 160. FIG. 6 depicts an embodiment showing a cross-sectional view of secondary pocket 160 on the top side of pocket member 110, with tab 161 in an undeployed state. In this embodiment, the top surface of secondary pocket 160 may include a Velcro® (e.g., a hook and loop fastener) surface that can fasten to attachment mechanism 150 (not shown in FIG. 6). In other embodiments, secondary pocket 160 and secondary strap 162 may be attached to the top surface of attachment mechanism 150 and be deployed after attachment mechanism 150 is connected to pocket member 110.

FIG. 7 depicts an embodiment of pressure bandage 100 that is wrapped around a patient to apply pressure to a left sided pacemaker ICD implant area (as in FIG. 4). In this embodiment, secondary strap 162 has been deployed to wrap under the left arm of the patient and connect to a portion of elastic band 140 at the patient's back (not shown in FIG. 7). In this embodiment, attachment mechanism 150 covers secondary pocket 160 when pressure bandage 100 is deployed over a wound area on a patient. In this state, secondary strap 162 helps ensure that additional inward pressure is exerted on an inferior aspect of the wound, and helps maintain optimal positioning of the pressure bandage 100. In various embodiments, attachment mechanism 150 may be connectable to the top surface of secondary pocket 160 whether secondary strap 162 is deployed or not.

When the pressure bandage 100 is used on a right sided pacemaker or ICD implant, secondary strap 162 can be pulled from the opposite opening 164 of secondary pocket 160. Strap 162 can be pulled across the right lateral chest area in a similar fashion to the above, and tab end member 161 can be rotated 180° for proper fixation to band 140 in the back.

The examples contained herein are offered by way of illustration and not by any way of limitation.

Although the invention has been described in some detail by way of illustration and example for purposes of clarity of understanding, it should be understood that certain changes and modifications may be practiced within the scope of the appended claims. Modifications of the above-described modes for carrying out the invention that would be understood in view of the foregoing disclosure or made apparent with routine practice or implementation of the invention to persons of skill in food chemistry, food processing, mechanical engineering, and/or related fields are intended to be within the scope of the following claims.

The invention claimed is:

1. A pressure bandage, comprising:
    an elastic band, comprising:
        a first end comprising a pocket member;
        a second end configured to be removably attached to the first end; and
        a shoulder strap configured to wrap around a shoulder of a patient and having a center component with a higher elasticity than a remainder of the shoulder strap, the center component of the shoulder strap being configured to engage the shoulder of the patient, and wherein the center component is located between a first edge and a second edge of the shoulder strap, and a region of lower elasticity than the center component surrounds the center component between the first edge and the second edge; and
        an inflatable bladder configured to be removably insertable into the pocket member and inflated to apply a first pressure to a wound area of the patient when inserted into the pocket member.

2. The pressure bandage of claim 1, wherein the elastic band has a top side and a bottom side, wherein the bottom side comprises a non-adhesive, absorptive material.

3. The pressure bandage of claim 2, wherein a bottom side of the pocket member at the first end of the elastic band comprises an expandable mesh.

4. The pressure bandage of claim 1, wherein the first pressure is about 20-40 mm Hg.

5. The pressure bandage of claim 1, wherein the wound area comprises the site of one of a pacemaker implant or an implantable cardioverter defibrillator implant.

6. The pressure bandage of claim 1, wherein the inflatable bladder is substantially rectangular in shape.

7. The pressure bandage of claim 6, wherein the inflatable bladder is approximately 5×6×2 inches when inflated.

8. The pressure bandage of claim 1, further comprising a tube element having a first end attached to the inflatable bladder and a second end comprising one of a 3-way stopcock, a valve, and a luer lock.

9. The pressure bandage of claim 1, wherein at least one of the first end and the second end of the elastic band further comprise at least one of a hook and loop fastener, a buckle, and a clip.

10. The pressure bandage of claim 1, further comprising:
    a secondary pocket attached to a top side of the pocket member, wherein the secondary has an open front end and an open back end; and
    an elastic secondary strap having a first end and a second end, wherein the first end of the elastic secondary strap is attached to the top side of the pocket member under the secondary pocket, the second end of the elastic secondary strap is removably attachable to at least a portion of a middle section of the elastic band.

11. The pressure bandage of claim 10, wherein the second end of the elastic secondary strap further comprises at least one of a hook and loop fastener, a buckle, and a clip.

12. The pressure bandage of claim 10, wherein the second end of the elastic secondary strap deployable through at least one of the open front end and the open back end.

13. A method of applying a pressure bandage to a patient, comprising:
    positioning a pocket member disposed in an elastic band over a wound area of the patient;
    wrapping a shoulder strap of the elastic band having a center component with a higher elasticity than a remainder of the shoulder strap around an ipsilateral shoulder of the patient, the center component being located between a first edge and a second edge of the shoulder strap, and a region of lower elasticity than the center component surrounding the center component between the first edge and the second edge;
    wrapping a portion of the elastic band diagonally around a back of the patient and then around a chest of the patient under a contralateral arm of the patient; and
    stretching the elastic band to attach an end of the elastic band to a surface over a top of the pocket member.

14. The method of claim 13, comprising inserting an inflatable bladder in the pocket member and inflating the inflatable bladder to a first pressure.

15. A pressure bandage, comprising:
    an elastic band comprising a first end having a pocket member, a second end configured to be removably attached to the first end, and a shoulder strap configured to wrap around a shoulder of a patient, wherein the shoulder strap comprises a center component configured to engage the shoulder of the patient, wherein the center component is located between a first edge and a second edge of the shoulder strap, and a region of lower elasticity than the center component surrounds the center component between the first edge and the second edge;
    a secondary pocket comprising a rectangular piece of material having two opposing edges attached to a top side of the pocket member, an open front edge unattached from the pocket member, and an open back edge unattached from the pocket member and opposing the open front edge; and a secondary strap having a first end attached to the top side of the pocket member under the secondary pocket, and a second end configured to be selectively deployed via the open front end or the open back end depending on a location of a wound of the patient.

16. The pressure bandage of claim 15, comprising an inflatable bladder configured to be removably insertable into the pocket member and inflated to apply a first pressure to the wound area of the patient when inserted into the pocket member.

17. The pressure bandage of claim 15, wherein the secondary strap is elastic.

* * * * *